United States Patent
Nicoll et al.

(10) Patent No.: US 10,507,178 B2
(45) Date of Patent: Dec. 17, 2019

(54) METHOD FOR TREATING INTERVERTEBRAL DISC DEGENERATION

(71) Applicant: Research Foundation of the City University of New York, New York, NY (US)

(72) Inventors: Steven B. Nicoll, New York, NY (US); Devika Varma, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 453 days.

(21) Appl. No.: 15/148,488

(22) Filed: May 6, 2016

(65) Prior Publication Data

US 2016/0324888 A1 Nov. 10, 2016

Related U.S. Application Data

(60) Provisional application No. 62/157,494, filed on May 6, 2015.

(51) Int. Cl.
| | |
|---|---|
| *A61F 2/08* | (2006.01) |
| *A61K 9/00* | (2006.01) |
| *A61K 31/132* | (2006.01) |
| *A61K 31/717* | (2006.01) |
| *A61K 33/04* | (2006.01) |
| *A61L 27/26* | (2006.01) |
| *A61L 27/50* | (2006.01) |
| *A61L 27/52* | (2006.01) |

(52) U.S. Cl.
CPC .......... *A61K 9/0019* (2013.01); *A61K 31/132* (2013.01); *A61K 31/717* (2013.01); *A61K 33/04* (2013.01); *A61L 27/26* (2013.01); *A61L 27/50* (2013.01); *A61L 27/52* (2013.01); *A61L 2400/06* (2013.01); *A61L 2430/38* (2013.01)

(58) Field of Classification Search
CPC .. A61B 1/00; A61F 2/0063; A61F 2002/2835; A61F 2002/2839; A61F 2002/30001; A61F 2002/30003; A61F 2002/30006; A61F 2002/30064
See application file for complete search history.

(56) References Cited

U.S. PATENT DOCUMENTS

| | | | |
|---|---|---|---|
| 9,193,948 B2 | 11/2015 | Nicoll et al. | |
| 2003/0138490 A1 | 7/2003 | Hu et al. | |
| 2005/0196377 A1 | 9/2005 | Ratcliffe et al. | |
| 2007/0098675 A1 | 5/2007 | Elisseeff et al. | |
| 2007/0110788 A1 | 5/2007 | Hissong et al. | |
| 2007/0269518 A1* | 11/2007 | Walline ................ | A61K 6/0052 424/484 |
| 2011/0182957 A1* | 7/2011 | Nicoll .................... | A61L 27/20 424/401 |

FOREIGN PATENT DOCUMENTS

WO 2009155583 12/2009

OTHER PUBLICATIONS

Malhotra, N. et al.: An Injectable Nucleus Pulposus Implant Restores Compressive Range of Motion in the Ovine Disc; Spine (Phila Pa 1976).; Aug. 15, 2012; pp. 1-15; vol. 37, Issue 18.
Smith, L. et al; In Vitro Characterization of a Stem-Cell-Seeded Triple-Interpenetrating-Network Hydrogel for Functional Regeneration of the Nucleus Pulposus; Tissue Engineering: Part A; Mar. 19, 2014; pp. 1841-1849; vol. 20, Nos. 13 and 14.
Showalter, B. et al.; Nucleotomy Reduces the Effects of Cyclic Compressive Loading with Unloaded Recovery on Human Intervertebral Discs; J Biomech.; Aug. 22, 2014; pp. 2633-2640; vol. 47, Issue 11.
Reza, A. et al; Characterization of novel photocrosslinked carboxymethylcellulose hydrogels for encapsulation of nucleus pulposus cells; Acta Biomaterialia; Jun. 6, 2009; pp. 179-186.
Reza, A. et al; Serum-Free, Chemically Defined Medium WithTGF-beta3 Enhances Functional Properties of Nucleus Pulposus Cell-Laden Carboxymethylcellulose Hydrogel Constructs; Biotechnology and Bioengineering; Feb. 1, 2010; pp. 384-395; vol. 105, No. 2; Wiley InterScience.
Stalling, S. et al. Development of photocrosslinked methylcellulose hydrogels for soft tissue reconstruction; Acta Biomaterialia; Feb. 20, 2009; pp. 1911-1918.
Gupta, M. et al.; Functional nucleus pulposus-like matrix assembly by human mesenchymal stromal cells is directed by macromer concentration in photocrosslinked carboxymethylcellulose hydrogels; Cell and Tissue Research; Aug. 5, 2014; pp. 527-539; vol. 358, No. 2; Springer.
Varma, D. et al.; Injectable carboxymethylcellulose hydrogels for soft tissue filler applications; Acta Biomaterialia; Aug. 23, 2014; pp. 4996-5004; vol. 10; Elsevier Ltd.
Lin, H. et al.; Lower crosslinking density enhances functional nucleus pulposus-like matrix elaboration by human mesenchymal stem cells in carboxymethylcellulose hydrogels; Society for Biomaterials; Aug. 25, 2015; Wiley Online Library.
Gold, G. et al.; Development of crosslinked methylcellulose hydrogels for soft tissue augmentation using an ammonium persulfate-ascorbic acid redox system; Carbohydrate Polymers; Aug. 4, 2015; pp. 497-507; vol. 134; Elsevier Ltd.

* cited by examiner

*Primary Examiner* — Micah Paul Young
(74) *Attorney, Agent, or Firm* — Peter J. Mikesell; Schmeiser, Olsen & Watts, LLP

(57) ABSTRACT

An injectable carboxymethylcellulose (CMC) and methylcellulose (MC) hydrogel derived from the plant-based polysaccharide, cellulose, is provided which gels in situ and repairs the intervertebral disc in the spinal column or other cartilaginous tissues. One specific application is for replacement of the nucleus pulposus (NP), the central gelatinous region of the intervertebral disc, following injury or degeneration.

11 Claims, 6 Drawing Sheets

|  | Sham | | | Repaired | | |
| --- | --- | --- | --- | --- | --- | --- |
|  | Intact | Injured | No implant | Intact | Injured | Implant |
| Compressive Stiffness (kN/mm) | 0.544 ± 0.156 | 0.582 ± 0.140 * | 0.604 ± 0.160 * | 0.543 ± 0.150 | 0.594 ± 0.132 * | 0.500 ± 0.126 $ |
| Tensile Stiffness (kN/mm) | 0.186 ± 0.038 | 0.170 ± 0.032 * | 0.172 ± 0.025 | 0.189 ± 0.041 | 0.174 ± 0.049 * | 0.192 ± 0.044 $ |
| Slow Ramp Stiffness (kN/mm) | 0.236 ± 0.057 | 0.262 ± 0.057 * | 0.275 ± 0.066 *, $ | 0.220 ± 0.062 | 0.247 ± 0.056 * | 0.209 ± 0.051 #, $ |

- * Sig diff wrt to intact
- $ Sig diff wrt to injured
- # sig diff wrt to no implant

FIG. 3

METHOD FOR TREATING INTERVERTEBRAL DISC DEGENERATION

CROSS-REFERENCE TO RELATED APPLICATIONS

This application claims priority to and is a non-provisional of U.S. Patent Application Ser. No. 62/157,494 (filed May 6, 2015), the entirety of which is incorporated herein by reference.

STATEMENT OF FEDERALLY SPONSORED RESEARCH OR DEVELOPMENT

This invention was made with government support under contract numbers CBET 0747968 and DMR 1207480 awarded by the National Science Foundation. The government has certain rights in the invention.

BACKGROUND OF THE INVENTION

The subject matter disclosed herein relates to methods of treating intervertebral disc degeneration (IVDD) and, in particular, to the use of hydrogels as a nucleus pulposus (NP) tissue replacement. IVDD is the most common diagnosis for lower back pain, a debilitating condition that annually affects 15-30% of the United States population, with associated annual costs of $194 billion. Typical conditions arising from IVDD include disc herniation, degenerative spondylolisthesis, spinal stenosis and degenerative disc disease. These conditions result from a complex combination of aging, trauma and unhealthy lifestyles. Discectomy, which involves removal of NP tissue, is employed when non-operative treatments fail to alleviate pain. Although discectomy often provides immediate pain relief, it does not restore disc biomechanical function due to loss in disc height and intradiscal pressure. Lumbar discectomy is the most common surgery for herniated discs, during which portions of the NP are resected to decompress affected nerve roots. However, this treatment has a high recurrence rate (5-15%), and frequently requires secondary intervention. Additionally, the void space caused by NP removal leads to lower disc height, and subsequently more back pain. For heavily degenerated discs, spinal fusion is typically used, however, altered load distribution over time produces damage to adjacent discs. Thus, current treatment options have been inadequate for long-term disease management.

NP replacements have been explored in order to avoid long-term complications post discectomy. Several acellular biomaterials have been commercially produced in the past decade, but have not necessarily advanced beyond the developmental stage or received Food and Drug Administration (FDA) clearance for use in the United States. Although these NP replacements have been shown to redistribute loads and are less invasive than total disc replacements, several complications have been reported. These include extrusion of the material through the annulus, wear debris, and fatigue or fracture failure of cartilaginous endplates. Also, most of these materials fail to conform to the unique geometry of the NP and do not support cell encapsulation. For example, in vitro characterization of photo-crosslinked methacrylated carboxymethylcellulose (CMC) hydrogels demonstrated that these materials possess functional properties comparable to native NP and support stem cell differentiation towards an NP phenotype. A recent advance employed redox crosslinking, thereby providing an important step in the development of an injectable CMC hydrogel formulation amenable to clinical translation. However, injection of the CMC/redox initiator mixture into large bovine motion segments resulted in extravasation of the polymer solution and limited polymerization within the disc. Thus, improved hydrogel formulations are desired to enable stable polymerization.

The discussion above is merely provided for general background information and is not intended to be used as an aid in determining the scope of the claimed subject matter.

BRIEF DESCRIPTION OF THE INVENTION

An injectable carboxymethylcellulose (CMC) and methylcellulose (MC) hydrogel derived from the plant-based polysaccharide, cellulose, is provided which gels in situ and repairs the intervertebral disc in the spinal column or other cartilaginous tissues. One specific application is for replacement of the nucleus pulposus (NP), the central gelatinous region of the intervertebral disc, following injury or degeneration. An advantage that may be realized in the practice of some disclosed embodiments of the method is that the hydrogel polymerizes in situ and does not exhibit undesirable extrusion.

In a first embodiment a method for providing therapeutic benefit to a patient is provided. The method comprising injecting a composition of matter between a first bone and a second bone of a patient, the composition of matter comprising methacrylated carboxymethylcellulose (CMC) and methacrylated methylcellulose (MC), wherein the patient has a body temperature of at least 33° C.; and permitting the composition of matter to undergo thermal gelation at the body temperature of the patient, thereby forming a hydrogel between the first bone and the second bone.

In a second embodiment, a method for providing therapeutic benefit to a patient experiencing intervertebral disc degeneration is provided. The method comprising removing nucleus pulposus (NP) tissue from between a first vertebra and a second vertebra of a patient; injecting a composition of matter between the first vertebra and the second vertebra of the patient, the composition of matter comprising methacrylated carboxymethylcellulose (CMC) and methacrylated methylcellulose (MC), wherein the methacrylated methylcellulose is a mix of a first methacrylated methylcellulose with a first molecular weight below about 20 kDa and a second methacrylated methylcellulose with a second molecular weight above about 30 kDa, the mix being at less than 8% (w/v) concentration, wherein the patient has a body temperature of at least 33° C.; and permitting the composition of matter to undergo thermal gelation at the body temperature of the patient, thereby forming a hydrogel between the first vertebra and the second vertebra.

In a third embodiment, a method for providing therapeutic benefit to a patient experiencing intervertebral disc degeneration is provided. The method comprising removing nucleus pulposus (NP) tissue from between a first vertebra and a second vertebra of a patient; injecting a composition of matter between the first vertebra and the second vertebra of the patient, the composition of matter comprising a redox initiator system, methacrylated carboxymethylcellulose (CMC) and methacrylated methylcellulose (MC), wherein the methacrylated methylcellulose is a mix of a first methacrylated methylcellulose with a first molecular weight below about 20 kDa and a second methacrylated methylcellulose with a second molecular weight above about 30 kDa, wherein the patient has a body temperature of at least 33° C.; and permitting the composition of matter to undergo thermal gelation and redox polymerization at the body temperature of the patient, thereby forming a hydrogel between the first vertebra and the second vertebra.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 3 is a table comparing additional biomechanical parameters of intact, injured and repaired motion segments in experimental and sham groups.

DETAILED DESCRIPTION OF THE INVENTION

Figure 1A:
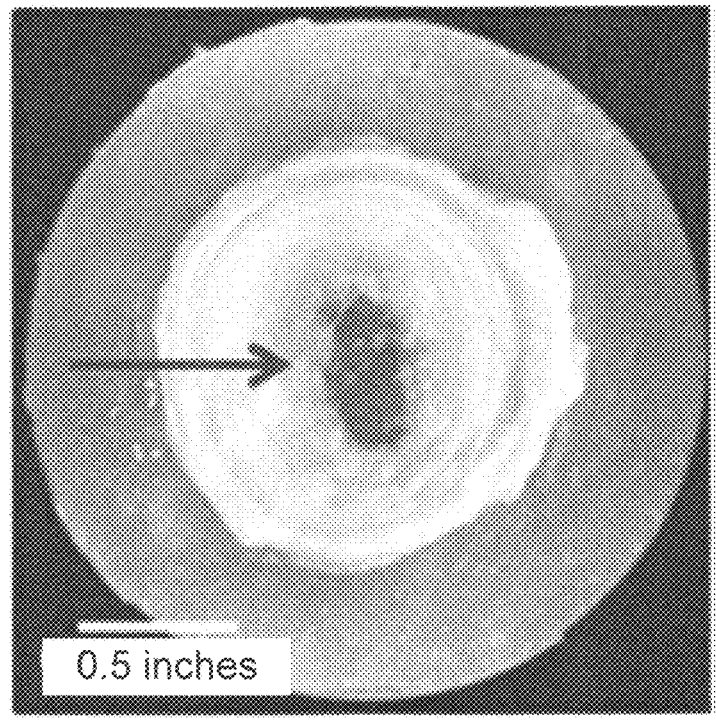
FIG. 1A is a transverse image of motion segments after repair.

This disclosure focuses on the use of plant-derived cellulosic polymers for engineering injectable nucleus pulposus (NP) replacements. Specifically, it employs a combination of methacrylated carboxymethylcellulose (CMC) and methacrylated methylcellulose (MC) optimized for in situ gelation in the disc space. The carboxyl groups on CMC are ionized at physiologic pH, similar to the anionic polysaccharides found in the native disc, and provide an environment more conducive to swelling, nutrient transport and extracellular matrix organization in comparison to inert polymers, such as poly(ethylene oxide). Increased hydrophobic interactions between the methoxy groups on MC afford thermogelation properties and increased viscosity above 33° C., which prevents extravasation of the material upon injection. Methacrylated methylcellulose (MC) is incorporated to create CMC-MC copolymers, capitalizing on the thermogelation property of MC to achieve higher viscosities at 37° C. The increased viscosity allows local retention of the injected material and subsequent curing in situ. Hence, an injectable, thermogelling, redox-crosslinked CMC-MC copolymer with material properties akin to the native nucleus pulposus (NP) is provided. The hydrogel implant restored disc height and native biomechanics of the bovine disc post nucleotomy.

Cellulose is the most abundant naturally occurring organic compound on the planet. Therefore, this novel material is renewable and a "green" alternative to synthetic polymers and animal-derived proteins and polysaccharides used for the repair of cartilaginous tissues. Further, cellulose derivatives are more cost-effective than other polysaccharides (e.g., chondroitin sulfate and hyaluronic acid) currently used for similar applications, and obviates risks associated with animal or bacterial by-products. In addition, the covalently crosslinked MC/CMC gels are not susceptible to enzymatic degradation by mucopolysaccharidases in humans (e.g., hyaluronidase), as the polysaccharides can only be cleaved by cellulase, an enzyme absent in humans. Still, the interchain ester crosslinks in the MC/CMC network are hydrolyzed in a controlled manner so as not to impede matrix elaboration and tissue development by incorporated cells.

Methacrylated methylcellulose (MC) and methacrylated carboxymethylcellulose (CMC) are combined to form an injectable nucleus pulposus replacement material. Specifically, MC and CMC were methacrylated as described in Stalling et al., *Acta Biomater.* 5:1911-18, 2009 and Reza et al., *Biotech. Bioeng.* 105:384-395, 2010. Briefly, a 1% (w/v) solution of 90 kDa CMC (Sigma) and a 1:1 mix of 14 kDa and 41 kDa MC (Sigma) were each reacted with a 40-fold excess of methacrylic anhydride (Sigma) in deionized water over 24 h at 4° C. and a pH of 8.0. The modified solutions were purified via dialysis for three days against deionized water to remove excess, unreacted methacrylic anhydride. The purified modified CMC and MC were recovered via lyophilization and the solid products were stored at −20° C. After acid hydrolysis of the purified methacrylated CMC and MC, the degree of modification was confirmed using $^1$H-NMR (300 MHz, Varian Mercury 300, Agilent Technologies). The methacrylation percentages ranged from 9% for MC to 25% for CMC.

To produce hydrogels, the 1:1 mix of methacrylated MC at a 3% (w/v) macromer concentration was added to a 3% (w/v) solution of 90 kDa methacrylated CMC in Dulbecco's phosphate buffered saline in dual-barrel syringes and mixed with ammonium persulfate (APS) (20 mM) and tetramethylethylenediamine (TEMED) (20 mM) in separate syringe barrels. The APS/TEMED redox initiation system provides for free radical polymerization without the need for UV light (Stalling et al., *Acta Biomater.* 5:1911-18, 2009; Reza et al., *Biotech. Bioeng.* 105:384-395, 2010). Examples of redox initiator systems include ammonium persulfate and tetramethyl-ethylenediamine at a concentration of, for example, 20 mM.

As a proof of principle, the MC/CMC redox-crosslinked gels were injected into bovine discs post nucleotomy to determine if they could restore tissue material properties. Importantly, the MC/CMC implant was able to restore parameters associated with NP integrity without AF repair (specifically, the neutral zone stiffness and the range of motion), and did not herniate or extrude. Also, the disc height, suggestive of the level of hydration and hydrostatic pressure, was restored with repair. The MC was combined with the CMC component because of its thermogelling behavior above 33° C., which allows the initiators to remain localized upon injection at body temperature (37° C.) and not diffuse away. As such, they initiate the free radical polymerization and interchain covalent crosslinking via the methacrylate groups. The thermogelling MC component was an important addition allowing the hydrogel to remain localized within the disc tissue for curing in situ. The specific formulation of CMC-MC was based on optimization of injectability, gelation and material properties. The $E_y$ and Swelling ratio ($Q_w$) of the gels were comparable to values for native NP tissue (about 5 kPa and about 19, respectively). As used in this specification, the term "about" means within 5%. Thermogelling alone is not sufficient to form a suitable structural material but is effective in keeping the initiators at the injection site, preventing extravasation.

When methacrylated CMC was injected alone (at either 90 kDa or 250 kDa) with the initiators into the bovine intervertebral disc, gelation did not occur. In addition, the specific MC formulation was used, a mix of a low (14 kDa) and medium (41 kDa) molecular weight (MW) polymer at 3% (w/v), because the low MW MC alone or a mix of the two at less than 3% did not undergo sufficient thermogelation to allow for crosslinking to proceed. Also, the medium MW MC was too viscous to use alone and was therefore mixed with the lower MW MC (at 1:1). U.S. Patent publication US20110182957, international patent publication WO2009155583 and U.S. provisional applications 61/129,338 (filed Jun. 19, 2008) and 61/114,034 (filed Nov. 12, 2008) describe the use of methacrylated MC and CMC for plastic and reconstructive surgery and cartilaginous tissue repair. The content of each of these patent publications and patent applications is hereby incorporated by reference. In one embodiment, the methacrylated methylcellulose has a molecular weight below about 20 kDa and the second methacrylated methylcellulose is above about 30 kDa with the mix being less than 8% (w/v). The two methacrylated methylcellulose may be in a 1:1 (w/w) ratio. In one embodiment, one of the methacrylated methylcellulose polymers is above about 30 kDa and below about 50 kDa. The carboxymethylcellulose may have a molecular weight between about 80 kDa and about 100 kDa and may be less than 8% (w/v) concentration.

Figure 1B:
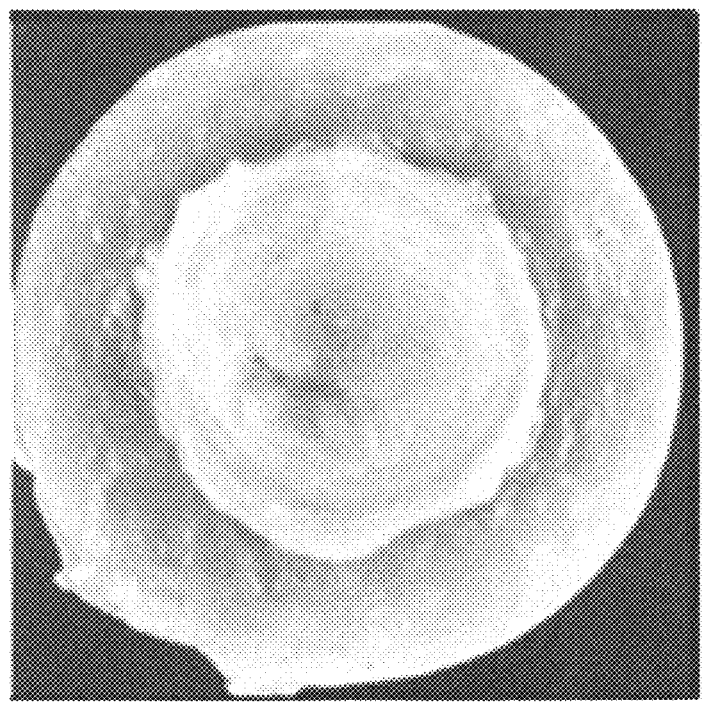
FIG. 1B is a transverse image of motion segments of a sham.
Figure 1C:
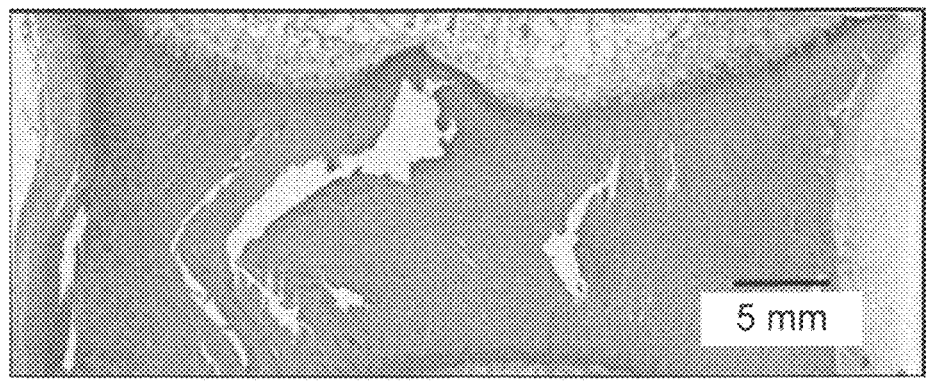
FIG. 1C is a histological section of an intact motion segment stained with toluidine blue.
Figure 1D:
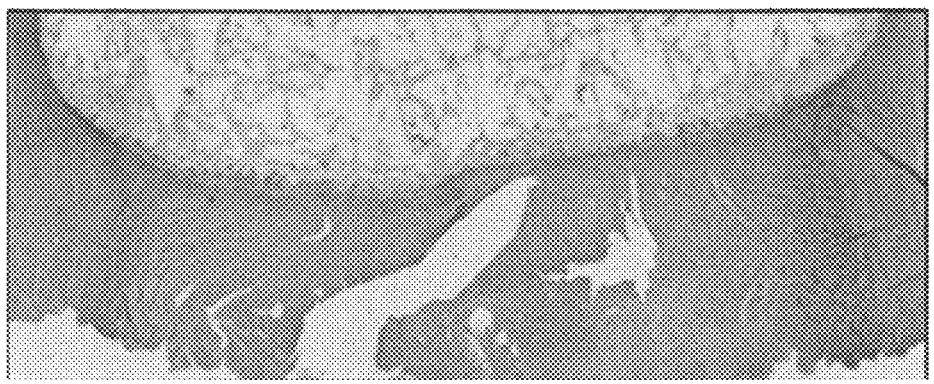
FIG. 1D is a histological section of an injured motion segment stained with toluidine blue.
Figure 1E:
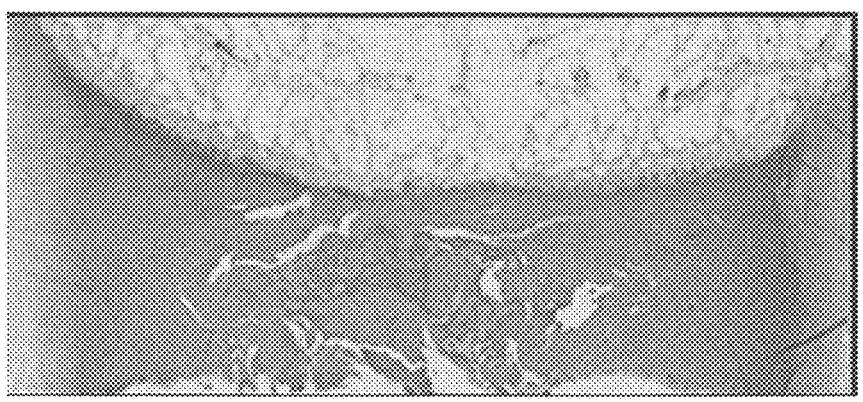
FIG. 1E is a histological section of a repaired motion segment stained with toluidine blue.
Figure 1F:
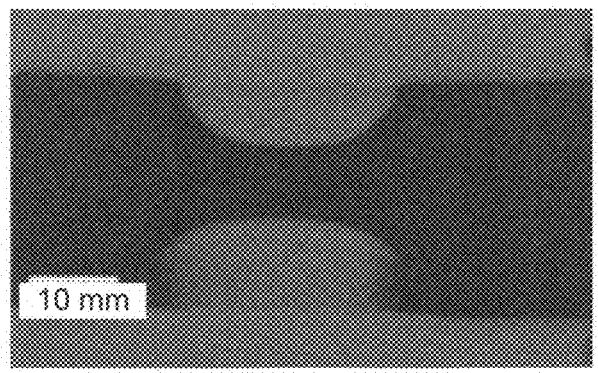
FIG. 1F is a sagittal radiograph of an intact motion segment.
Figure 1G:
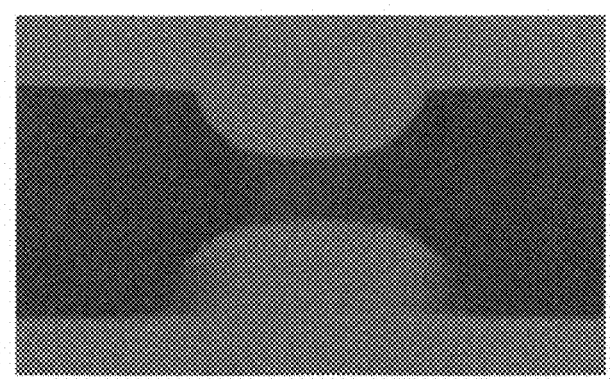
FIG. 1G is a sagittal radiograph of an injured motion segment.
Figure 1H:
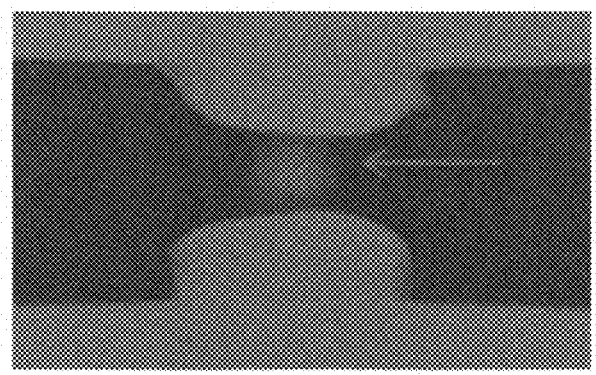
FIG. 1H is a sagittal radiograph of a repaired motion segment.

The CMC-MC hydrogels had a swelling ratio of 25.11±5.36, a Young's modulus ($E_y$) of 16.62±3.57 kPa and a percent relaxation of 33.83±3.11. The materials formed stable gels in situ (FIG. 1A, FIG. 1B, FIG. 1C, FIG. 1D, FIG. 1E) and restored disc height (FIG. 1F, FIG. 1G and FIG. 1H). FIG. 1A is a transverse image of the motion segments after mechanical testing post repair. The repaired sample in FIG. 1A shows the CMC-MC hydrogel (arrow). FIG. 1B is a sham shown for comparison. The sham sample in FIG. 1B exhibits a void NP. FIG. 1C shows a histological section of an intact motion segment stained with toluidine blue. FIG. 1D shows a histological section of an injured motion segment stained with toluidine blue. FIG. 1E shows a histological section of a repaired motion segment stained with toluidine blue indicating the CMC-MC hydrogel filling the void space (arrow). FIG. 1F shows a sagittal radiograph of an intact motion segment. FIG. 1G shows an injured motion segment. FIG. 1H shows a repaired motion segment with CMC-MC hydrogel visible with radiopaque dye (arrow).

Figure 2A:
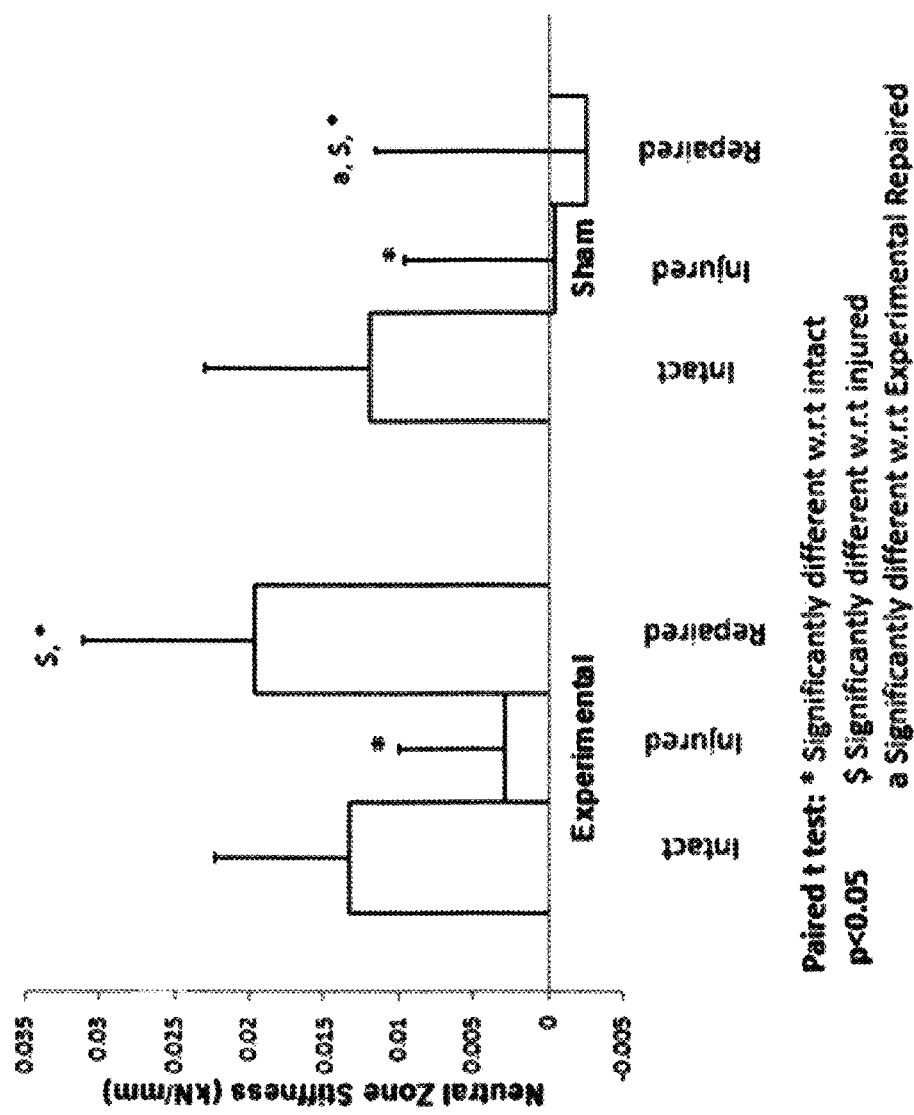
FIG. 2A is a graph comparing neutral zone (NZ) stiffness of intact, injured and repaired motion segments of experimental and sham groups.
Figure 2B:
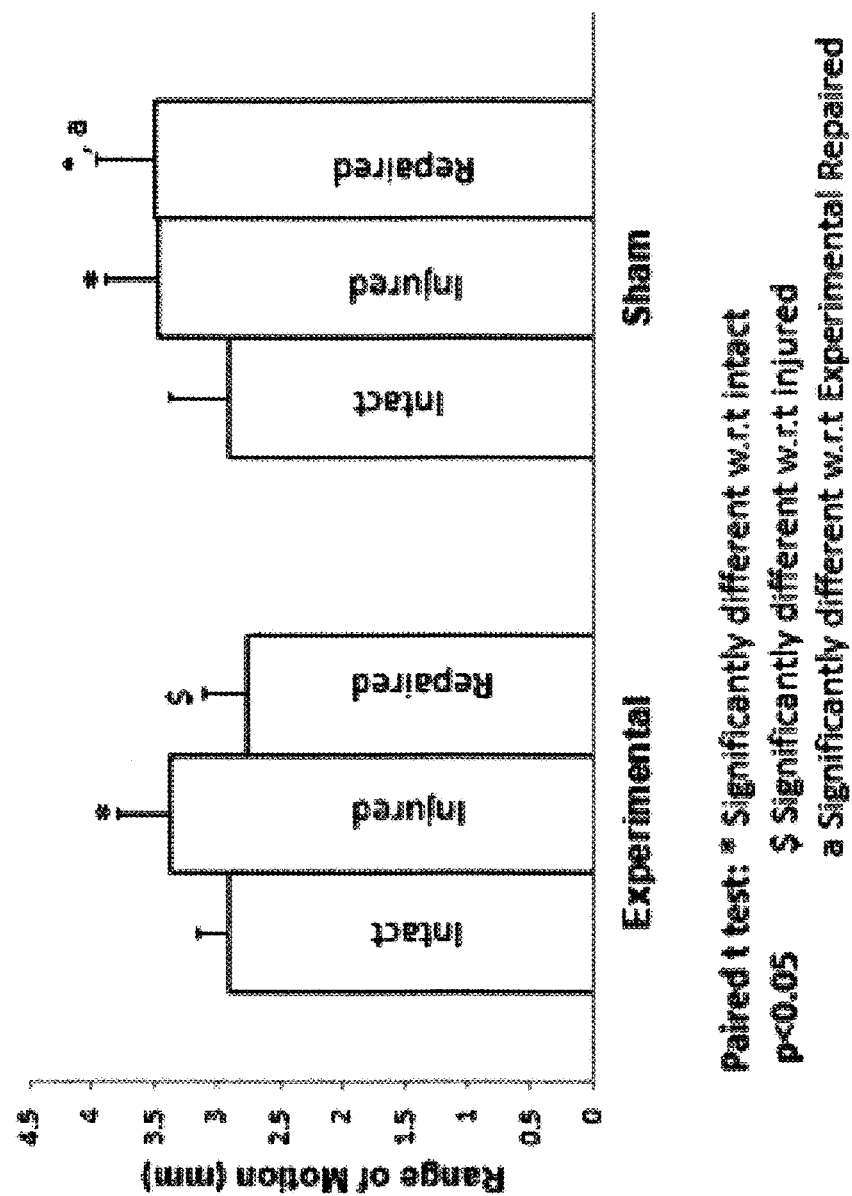
FIG. 2B is a graph comparing range of motion (ROM) of intact, injured and repaired motion segments of experimental and sham groups.

CMC-MC hydrogels restored several biomechanical parameters in bovine motion segments that were altered by nucleotomy (FIG. 3). There was a significant increase in the range of motion (ROM) as shown in FIG. 2B, compressive and slow-ramp stiffness, and a decrease in tensile and neutral zone stiffness in motion segments post nucleotomy compared to Intact samples (FIG. 3). Upon repair, the ROM, and compressive and slow-ramp stiffness significantly decreased with respect to Injured values, while the tensile and neutral zone (NZ) stiffness (see FIG. 2A) were significantly higher than Injured discs. All of these parameters for the Repaired condition were not significantly different from Intact values except for the NZ stiffness, which was higher than Intact specimens. Conversely, these properties were significantly different in the Sham repair with respect to Intact samples. The hydrogel implant did not extrude at any point during testing or incubation.

The CMC-MC hydrogels restored key biomechanical properties of the injured disc to intact values. The ROM and neutral zone have previously been found to be most dependent on NP integrity, while both NP and the annulus fibrosus (AF) impact the compressive, tensile and slow-ramp stiffness. The significant increase in the ROM and decrease in the NZ stiffness corroborated these findings. The compressive and slow-ramp stiffness were found to increase with removal of the NP, which suggests the transfer of load to the stiffer AF component of the disc. Along with the loss of NP tissue, nucleotomy resulted in destabilization of the AF and a significant decrease in tensile stiffness. Importantly, the CMC-MC implant was able to restore essential parameters associated with NP integrity without AF repair, and did not herniate or extrude. Interestingly, the NZ stiffness increased significantly post repair, which may be attributed to the higher $E_y$ of the CMC-MC gels (about 16 kPa) compared to native NP (about 5 kPa) and possible overfilling of the implant in the disc. Also, the disc height, suggestive of the level of hydration and hydrostatic pressure, was restored with repair.

Histological staining showed a mild foreign body reaction indicated by the formation of a thin fibrous capsule (less than 100 μm) when the CMC-MC solutions were injected subcutaneously in the dorsa of Sprague Dawley rats. The fibrous capsule thickness and composition around CMC-MC solutions injected subcutaneously, both without redox initiators and with 20 mM redox initiators, were characterized one month after implantation in vivo. Hematoxylin and eosin staining images depicted the fibrous capsule and the adjacent hydrogel. Alcian blue was used to stain the CMC-MC hydrogel while Picrosirius red highlighted the collagen fibers in the fibrous capsule. Minimal blue staining was indicative of remnants of the hydrogel in the CMC-MC formulation without initiators (0 mM). The fibrous capsule thickness around the redox-polymerized, CMC-MC hydrogels measured 77.76±28.45 μm, consistent with a mild foreign body reaction.

Methods

Polymer Synthesis and Material Characterization: Macromer synthesis: Methacrylation of 90 kDa CMC, and a low and medium viscosity blend of MC polymer was performed as previously described in *Acta Biomater*, 6:179-86, 2010. Hydrogel preparation: Solutions of CMC and MC in DPBS, both at 3% (w/v) macromer concentration, were prepared in dual-barrel syringes and mixed with ammonium persulfate (20 mM) and tetramethyl-ethylenediamine (20 mM) in separate syringe barrels.

In Situ Gelation: Motion segment preparation: Bone-disc-bone motion segments were harvested from skeletally mature bovine tails and frozen at $-20°$ C. until testing. Nucleotomy: Approximately 0.15-0.25 g of NP tissue was removed with a pituitary rongeur via a cruciate incision. In situ gelation protocol: CMC-MC solutions (containing trypan blue for visualization) were injected into the NP void with a 200 syringe needle. Post 30 minute incubation, the motion segments were dissected along the endplate and the hydrogel was carefully extracted.

Mechanical testing: Disks (3-mm diameter, about 2-mm thickness) were cored from extracted hydrogels and tested in unconfined compression to determine equilibrium Young's modulus ($E_y$) and % relaxation (n=7). Swelling ratio: Swelling ratio ($Q_w$) of hydrogels was measured at day 1 (n=7) after overnight incubation in DPBS at $37°$ C.

Biomechanical Restoration Post Nucleotomy: Study design and specimen preparation: Seven bovine tails were used for the study with two motion segments per tail assigned to an experimental and a sham group. Each motion segment underwent a mechanical loading regimen under Intact, Injured and Repaired/Sham conditions with repeated measures design to eliminate variations between animals and disc levels. Motion segments were potted in poly(methyl methacrylate). The height and average diameters were determined via X-Ray imaging and caliper measurements, respectively. For repair, CMC-MC solutions were injected into the void space of the injured disc with a radiopaque dye to visualize implant location. Mechanical testing: Mechanical testing was performed on an MTS Bionix Servohydraulic Test system in a saline DPBS bath. Samples underwent an initial 30 N preload followed by 25 cycles of tension-compression at 0.1 Hz between $-0.5$ MPa and 0.25 MPa with a final slow ramp from 0 to 170 N at 1 N per second. Analyses: The 25th cycle of cyclic loading was used for data analysis to ensure dynamic equilibrium was attained. Range of Motion (ROM) was calculated as peak-to-peak displacement. Neutral zone (NZ) stiffness was calculated as described in *J. Biomech*, 47:2633-40, 2014. The compressive and tensile stiffness were calculated from a linear regression of the load-displacement curve between 60-100% and 80-100% of the maximum load, respectively. A linear regression of the slow ramp load-displacement curve was used to obtain the slow ramp compressive stiffness. Statistical analysis: Data are presented as the mean±s.d. Student's paired t-tests were performed to compare biomechanical properties between all paired combinations (i.e., Injured vs. Repaired) ($p<0.05$ considered significant).

The injectable cellulosic hydrogels could also be used for dermal fillers (soft tissue augmentation), treatment of myocardial infarction, post-operative adhesion prevention, or for drug delivery.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for providing therapeutic benefit to a patient experiencing soft tissue damage between a first bone and a second bone, the method comprising:
    injecting a composition of matter between the first bone and the second bone of a patient, the composition of matter comprising methacrylated carboxymethylcellulose (CMC), methacrylated methylcellulose (MC), and a polymerization initiator, wherein the patient has a body temperature of at least $33°$ C.;
    permitting the composition of matter to undergo thermal polymerization at the body temperature of the patient, thereby forming a hydrogel between the first bone and the second bone;
    wherein the methacrylated methylcellulose (MC) is a mix of a first methacrylated methylcellulose with a first molecular weight below about 20 kDa and a second methacrylated methylcellulose with a second molecular weight above about 30 kDa, the mix being at least 3% (w/v) concentration and less than 8% (w/v) concentration, the first methacrylated methylcellulose and the second methacrylated methylcellulose being in about a 1:1 (w/w) ratio;
    wherein the methacrylated carboxymethylcellulose (CMC) has a molecular weight between about 80 kDa and about 100 kDa and is at least 3% (w/v) and less than 8% (w/v) concentration;
    wherein the methacrylated methylcellulose (MC) and the methacrylated carboxymethylcellulose (CMC) are present in a 1:1 (w/w) ratio.

2. The method as recited in claim 1, wherein the second molecular weight is above about 30 kDa and below about 50 kDa, the mix being at less than 8% (w/v) concentration.

3. The method as recited in claim 1, wherein the methacrylated methylcellulose is a mix of a 14 kDa methacrylated methylcellulose and a 41 kDa methacrylated methylcellulose at about 3% (w/v) concentration.

4. The method as recited in claim 1, wherein the methacrylated carboxymethylcellulose has a molecular weight of 90 kDa at about 3% (w/v) concentration.

5. The method as recited in claim 1, wherein the methacrylated methylcellulose is modified with methacrylate groups at a modification percentage of about 3-10% and the methacrylated carboxymethylcellulose is modified with methacrylate groups at a modification percentage of about 8-25%.

6. A method for providing therapeutic benefit to a patient experiencing intervertebral disc degeneration, the method comprising:
    removing nucleus pulposus (NP) tissue from between a first vertebra and a second vertebra of a patient;
    injecting a composition of matter between the first vertebra and the second vertebra of the patient, the composition of matter comprising methacrylated carboxymethylcellulose (CMC), methacrylated methylcellulose (MC) and a polymerization initiator, wherein the patient has a body temperature of at least $33°$ C.;
    wherein the methacrylated methylcellulose (MC) is a mix of a first methacrylated methylcellulose with a first molecular weight below about 20 kDa and a second methacrylated methylcellulose with a second molecular weight above about 30 kDa, the mix being at least 3% (w/v) concentration and less than 8% (w/v) concentration, the first methacrylated methylcellulose and the second methacrylated methylcellulose being in about a 1:1 (w/w) ratio;

wherein the methacrylated carboxymethylcellulose (CMC) has a molecular weight between about 80 kDa and about 100 kDa and is at least 3% (w/v) and less than 8% (w/v) concentration;

wherein the methacrylated methylcellulose (MC) and the methacrylated carboxymethylcellulose (CMC) are present in a 1:1 (w/w) ratio;

permitting the composition of matter to undergo thermal gelation at the body temperature of the patient, thereby forming a hydrogel between the first vertebra and the second vertebra.

7. The method as recited in claim 6, wherein the hydrogel has an equilibrium Young's modulus ($E_y$) of about 5 kPa.

8. The method as recited in claim 6, wherein the polymerization initiator is a redox initiator.

9. The method as recited in claim 8, wherein the redox initiator is selected from the group consisting of ammonium persulfate, tetramethyl-ethylenediamine and combinations thereof.

10. The method as recited in claim 9, wherein the redox initiator is present in a concentration of about 20 mM.

11. A method for providing therapeutic benefit to a patient experiencing intervertebral disc degeneration, the method comprising:

removing nucleus pulposus (NP) tissue from between a first vertebra and a second vertebra of a patient;

injecting a composition of matter between the first vertebra and the second vertebra of the patient, the composition of matter comprising a redox initiator, methacrylated carboxymethylcellulose (CMC) and methacrylated methylcellulose (MC), wherein the patient has a body temperature of at least 33° C.;

wherein the methacrylated methylcellulose (MC) is a mix of a first methacrylated methylcellulose with a first molecular weight below about 20 kDa and a second methacrylated methylcellulose with a second molecular weight above about 30 kDa, the mix being at least 3% (w/v) concentration and less than 8% (w/v) concentration, the first methacrylated methylcellulose and the second methacrylated methylcellulose being in about a 1:1 (w/w) ratio;

wherein the methacrylated carboxymethylcellulose (CMC) has a molecular weight between about 80 kDa and about 100 kDa and is at least 3% (w/v) and less than 8% (w/v) concentration;

wherein the methacrylated methylcellulose (MC) and the methacrylated carboxymethylcellulose (CMC) are present in a 1:1 (w/w) ratio;

permitting the composition of matter to undergo thermal gelation and redox polymerization at the body temperature of the patient, thereby forming a hydrogel between the first vertebra and the second vertebra.

\* \* \* \* \*